United States Patent [19]

Marshall

[11] 4,318,927

[45] Mar. 9, 1982

[54] METHOD OF PRODUCING LOW CALORIE ALCOHOLIC BEVERAGE WITH STARCH-DEGRADING ENZYMES DERIVED FROM *CLADOSPORIUM RESINAE*

[75] Inventor: James J. Marshall, Miami, Fla.

[73] Assignee: Lifeline Products, Inc., Plainfield, N.J.

[21] Appl. No.: 159,950

[22] Filed: Jun. 16, 1980

Related U.S. Application Data

[60] Division of Ser. No. 46,482, Jun. 7, 1979, Pat. No. 4,234,686, which is a continuation-in-part of Ser. No. 892,747, Apr. 3, 1978, Pat. No. 4,211,842.

[51] Int. Cl.$^3$ .............................................. C12C 11/04
[52] U.S. Cl. ........................................ 426/11; 426/16
[58] Field of Search ........................ 426/11, 13, 14, 16

[56] References Cited

U.S. PATENT DOCUMENTS

| | | | |
|---|---|---|---|
| 3,852,495 | 12/1974 | Schimpf | 426/14 |
| 3,988,204 | 10/1976 | Andreasen et al. | 435/205 X |
| 4,169,013 | 9/1979 | Smith et al. | 435/205 |

*Primary Examiner*—Lionel M. Shapiro
*Attorney, Agent, or Firm*—Cooper, Dunham, Clark, Griffin & Moran

[57] ABSTRACT

A culture filtrate of *Cladosporium resinae* (Strain ATCC No. 20495) has been found to contain a mixture of starch-degrading enzymes capable of bringing about efficient conversion of starch and pullulan into glucose. Culture conditions resulting in optimal production of the pullulan degrading activity been established. The amylolytic enzyme preparation obtained by culturing the fungus under these optimal conditions has been fractionated by ion-exchange and molecular sieve chromatography and shown to contain at least four enzymes, a maltase, α-amylase and two glucoamylase-type enzymes including a novel exo-pullulanase. The maltase and glucoamylase enzymes have been purified to homogeneity and their substrate specificity investigated. Both the mixture and the exo-pullulanase can be used in the manufacture of dextrose from starch. Alone or in conjunction with appropriate other starch-degrading enzymes the mixture or the exo-pullulanase may be used in the production of specific starch conversion products, including fructose syrups. Both the mixture and the exo-pullanase are useful in increasing the fermentability of high DE starch conversion products and may be useful in the production of low calorie alcoholic beverages.

4 Claims, 11 Drawing Figures

PRODUCTION OF EXO-STARCH AND PULLULAN DEGRADING ENZYMES BY C.RESINAE GROWN IN LIQUID CULTURE ON STARCH PLUS GLUCOSE (0.5%) (0.3%)

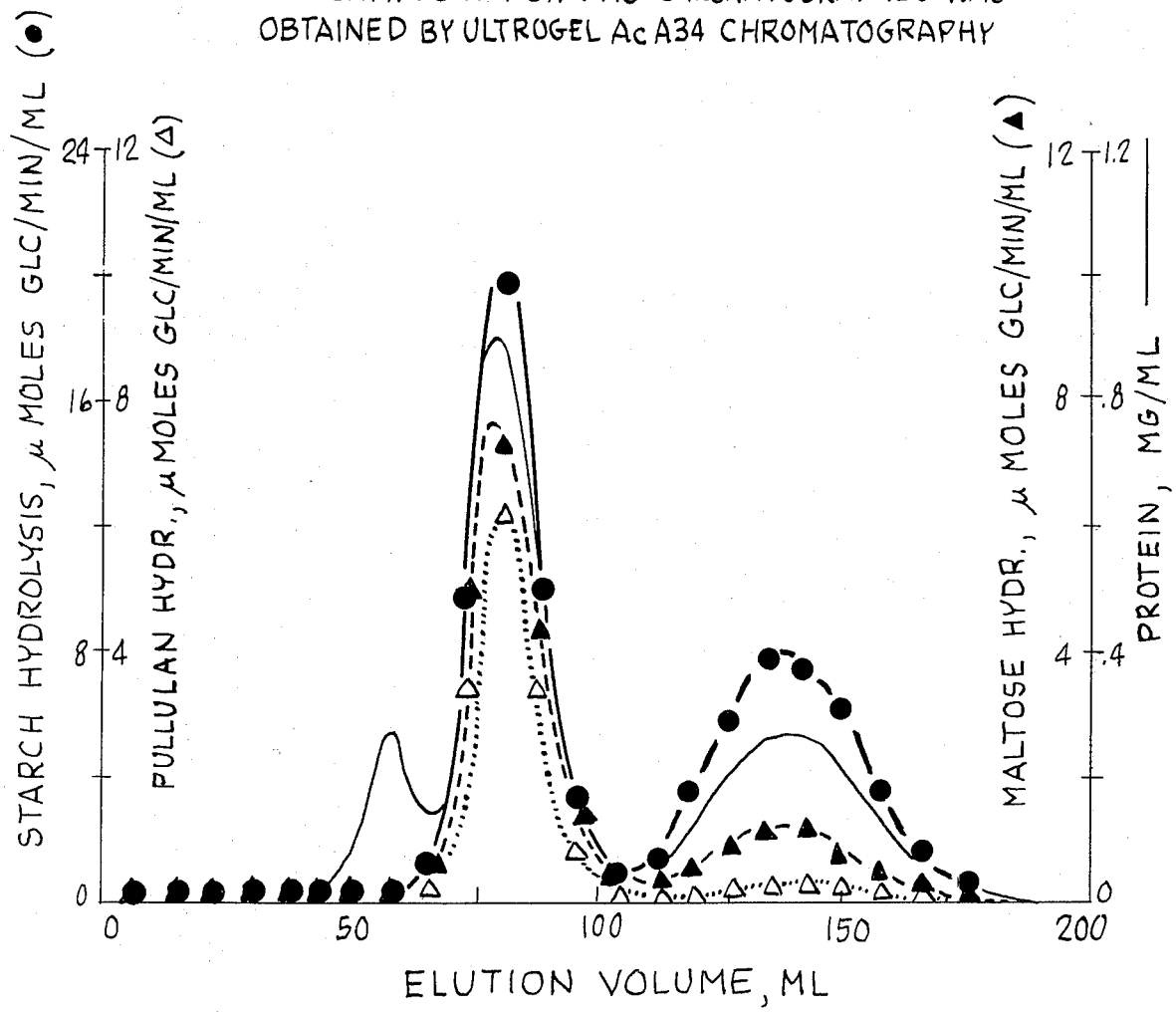

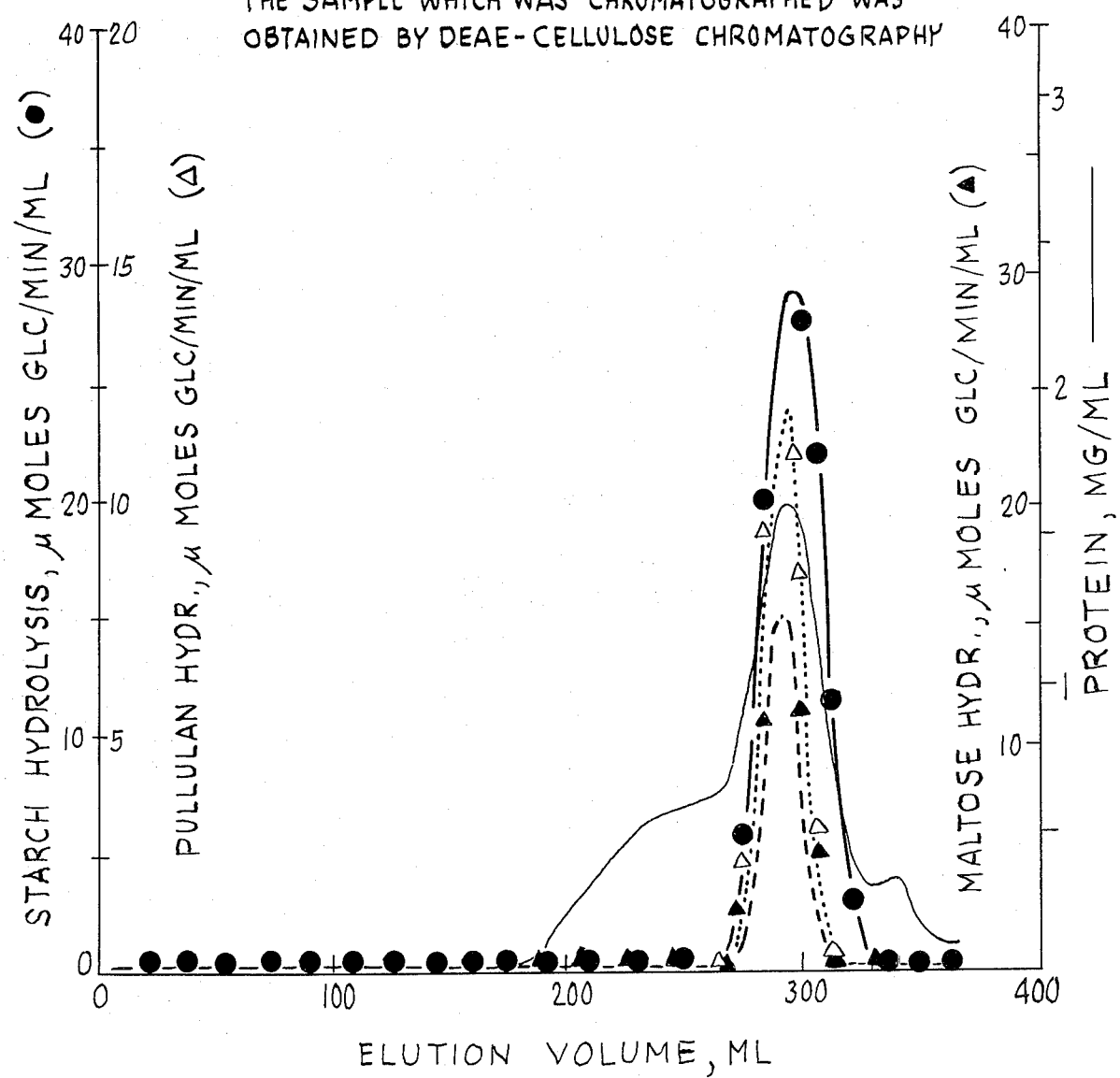

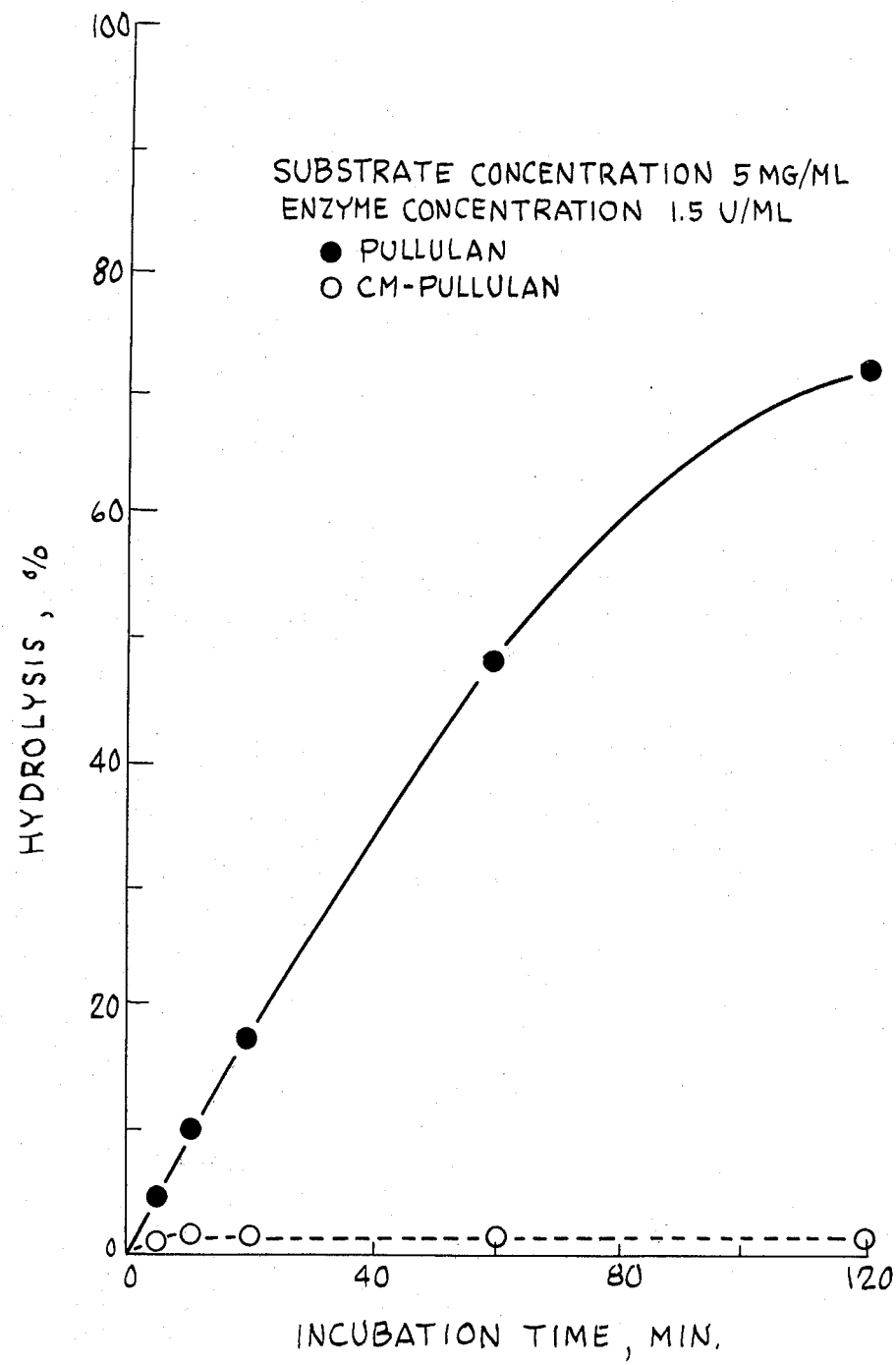

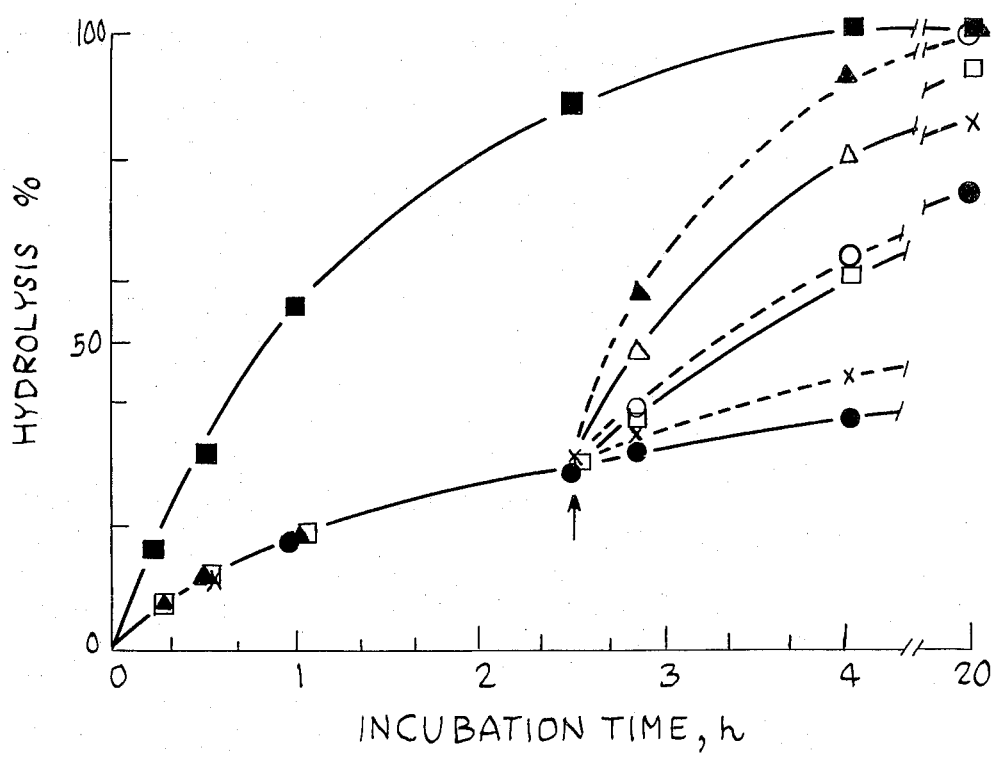

Fig. 6.

HYDROLYSIS OF β-LIMIT GLYCOGEN BY GLUCOAMYLASES

SUBSTRATE CONCENTRATION 10MG/ML
TEMPERATURE —37°C
FIGURE SHOWS HYDROLYSIS BY:

■ CLADOSPORIUM EXO-PULLULANASE (0.75 U/ML)
● ASPERGILLUS GLUCOAMYLASE II (1.5 U/ML)
× ASPERGILLUS GLUCOAMYLASE II (1.5 U/ML) + ASPERGILLUS GLUCOAMYLASE II (1.5 U/ML)
○ ASPERGILLUS GLUCOAMYLASE II (1.5 U/ML) + CLADOSPORIUM EXO-PULLULANASE (0.15 U/ML)
△ ASPERGILLUS GLUCOAMYLASE II (1.5 U/ML) + CLADOSPORIUM EXO-PULLULANASE (0.30 U/ML)
▲ ASPERGILLUS GLUCOAMYLASE II (1.5 U/ML) + CLADOSPORIUM EXO-PULLULANASE (0.75 U/ML)
□ ASPERGILLUS GLUCOAMYLASE II (1.5 U/ML) + CLADOSPORIUM GLUCOMYLASE S (0.75 U/ML)

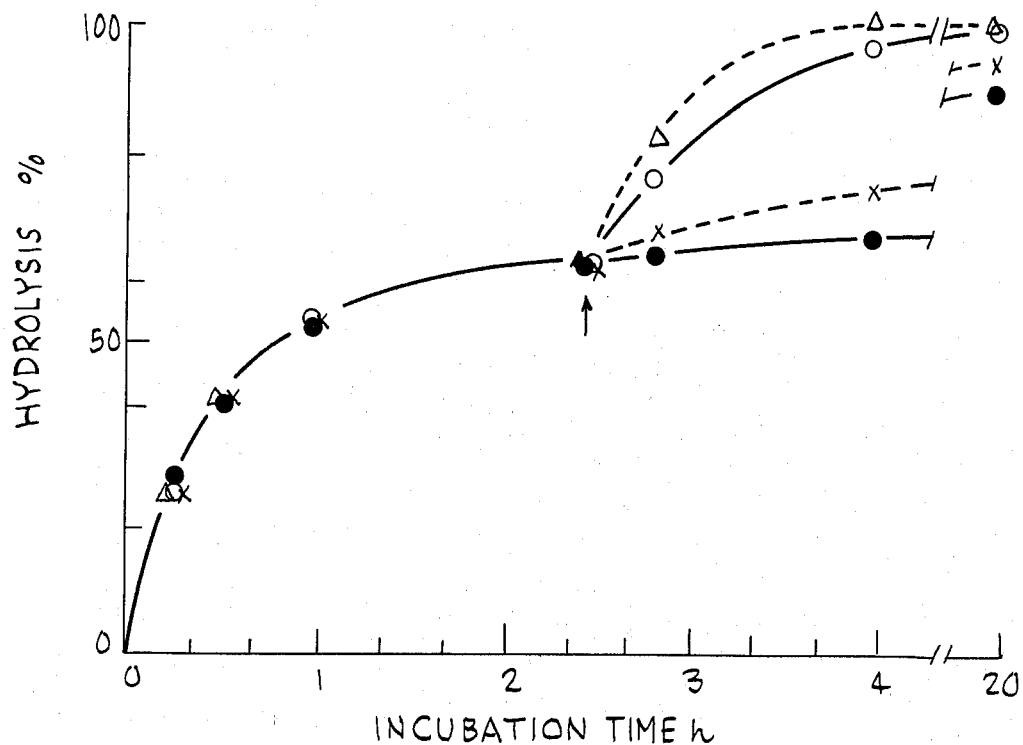

Fig. 7.

HYDROLYSIS OF GLYCOGEN BY GLUCOAMYLASES

SUBSTRATE CONCENTRATION : 10 MG/ML
TEMPERATURE : 37°C
FIGURE SHOWS HYDROLYSIS BY:
● ASPERGILLUS GLUCOAMYLASE II (1.5 U/ML)
X ASPERGILLUS GLUCOAMYLASE II (1.5 U/ML)+ASPERGILLUS GLUCOAMYLASE II (1.5 U/ML)
O ASPERGILLUS GLUCOAMYLASE II (1.5 U/ML)+CLADOSPORIUM GLUCOAMYLASE S (0.75 U/ML)
△ ASPERGILLUS GLUCOAMYLASE II (1.5 U/ML)+CLADOSPORIUM EXO-PULLULANASE (0.75 U/ML)

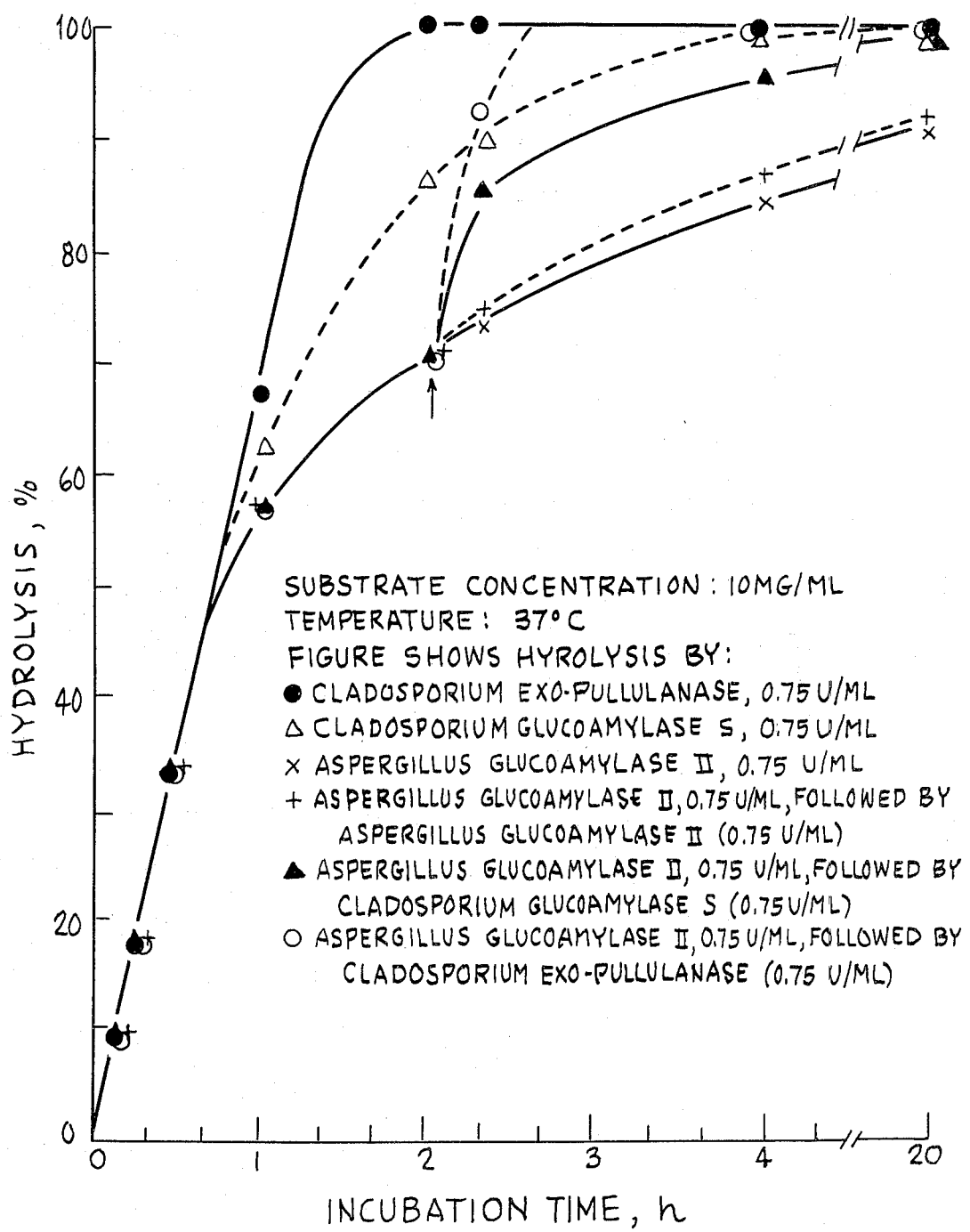

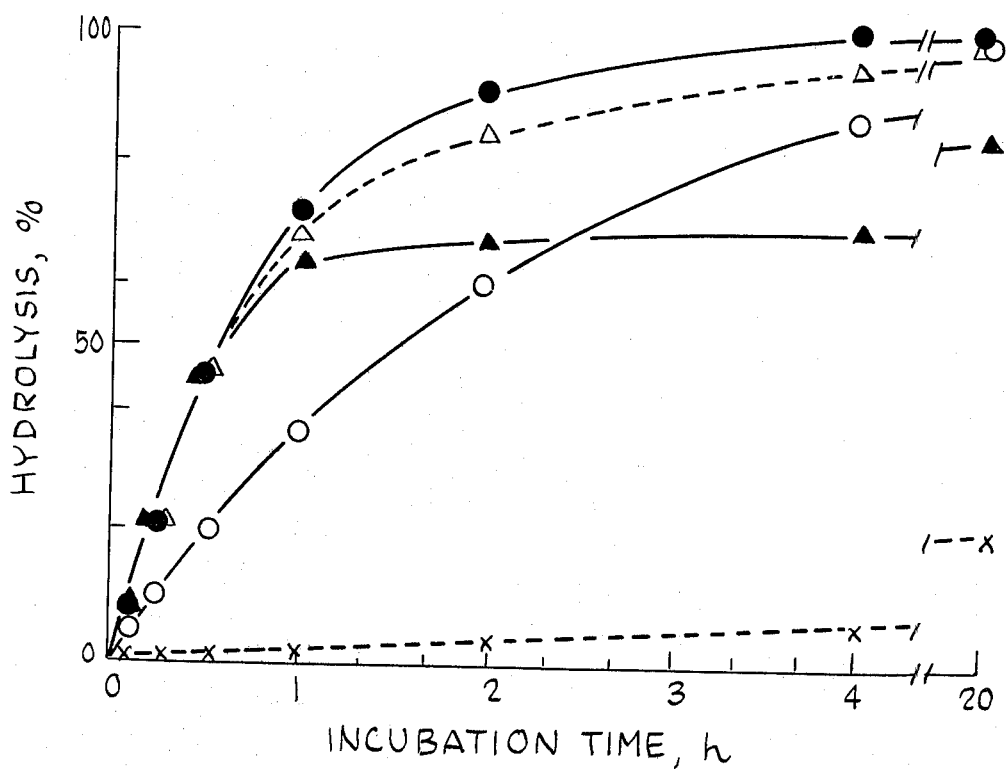

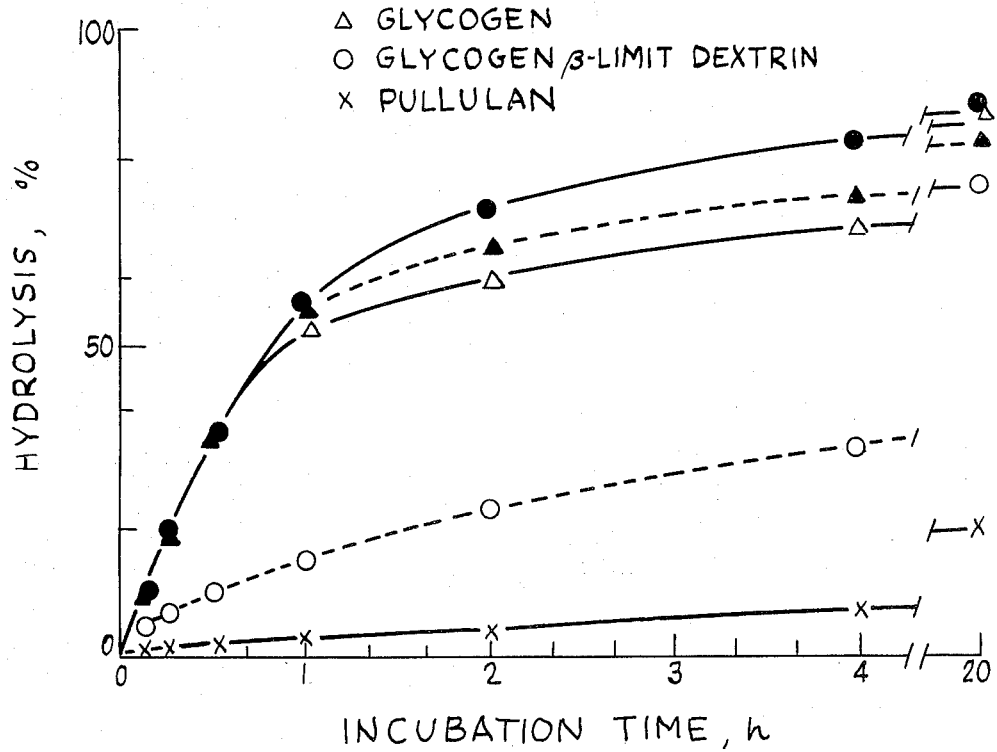

HYDROLYSIS OF α-GLUCANS BY C. RESINAE EXO-PULLULANASE

METHOD OF PRODUCING LOW CALORIE ALCOHOLIC BEVERAGE WITH STARCH-DEGRADING ENZYMES DERIVED FROM *CLADOSPORIUM RESINAE*

This is a division of application Ser. No. 046,482 filed June 7, 1979, now U.S. Pat. No. 4,234,686 issued Nov. 18, 1980, which in turn is a continuation-in-part of application Ser. No. 892,747 filed Apr. 3, 1978, now U.S. Pat. No. 4,211,842 issued July 8, 1980.

BACKGROUND OF THE INVENTION

At present the degradation of starch to dextrose involves enzymatic degradation using a glucoamylase derived from *Aspergillus niger*. However, there are several disadvantages associated with the use of the *Aspergillus* glucoamylase. Thus, for example, the degradation reaction is hindered by the branch points in the starch substrate; yields are often lower than desirable; by-products, notably isomaltose, are usually produced and substantially complete conversion requires a substantial time.

There has therefore been a need for a more efficient enzyme preparation and/or system useful in the production of dextrose from starch. To meet this need the present invention provides several enzymes including an exo-pullulanase which singly or as components of a mixture are useful in the enzymatic degradation of starch to dextrose.

BRIEF SUMMARY OF THE INVENTION

The present invention relates to an extremely efficient mixture of starch degrading enzymes produced by a strain of *Cladosporium resinae* (ATCC No. 20495). The invention further concerns the enzyme components of this mixture including a glucoamylase referred to herein as exo-pullulanase which rapidly hydrolyzes pullulan and isomaltose demonstrating its ability to readily cleave α-1,6 glucosidic linkages. Other components of this mixture are a second glucoamylase referred to herein as glucoamylase S, a maltase (α-glucosidase) and an α-amylase.

Additional aspects of this invention concern methods of culturing the microorganism and of recovering the mixture and individual components thereof. Finally, the present invention concerns methods of producing dextrose and/or other starch conversion products using the mixture of starch-degrading enzymes and/or the individual component enzymes including the exo-pullulanase.

Accordingly, it is one object of the present invention to provide a method of producing a mixture of starch-degrading enzymes from *Cladosporium resinae* (ATCC No. 20495).

It is a related object to provide this mixture of starch-degrading enzymes useful in the production of dextrose from starch.

A further object is to provide methods of producing the individual enzyme components of this mixture including exo-pullulanase.

A related object is to provide the individual enzymes which are components of this mixture including specifically exopullulanase.

Another object is to provide methods for utilizing the mixture of starch-degrading enzymes and the individual enzyme components in the production of dextrose from starch and in other starch conversion processes.

A final object of this invention is to provide an improved method for preparing low calorie alcoholic beverages.

How these and other objects of this invention are accomplished will become clear upon reading the accompanying detailed description of the invention and the claims which follow thereafter.

DETAILED DESCRIPTION OF THE INVENTION

Figure 1:
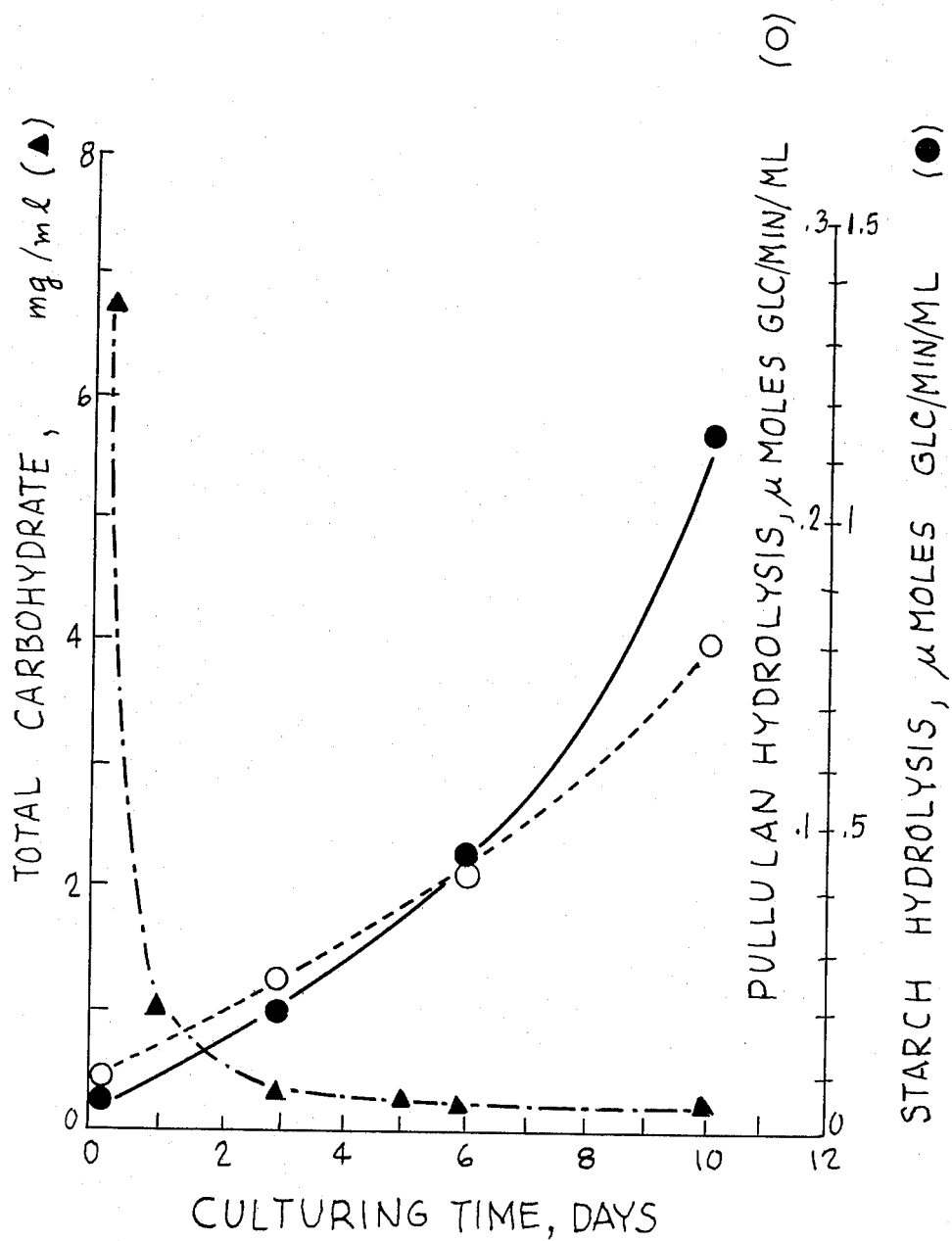

A species of *Cladosporium resinae* (Strain ATCC No. 20495) has been identified which produces at least four starch-degrading enzymes possessing a particularly high pullulanase activity relative to its amylase activity. A mixture of starch-degrading enzymes can be recovered from the microorganism after it has been cultivated on a suitable growth medium which contains an assimilable carbon source and other nutrients. Starch, glucose and maltose are suitable carbon sources although use of pullulan as the carbon source results in optimal production of one component of the enzyme mixture, namely, a novel glucoamylase referred to herein as exo-pullulanase.

Suitable media for culturing the fungus include a substantially liquid medium which includes the following:

|  | GRAMS PER LITER |
|---|---|
| $NH_4NO_3$ | 0.01–10.0 |
| $MgSO_4 \cdot 7H_2O$ | 0.03–3.0 |
| $KH_2PO_4$ | 0.15–12.5 |
| Yeast extract[1] | 0.001–0.1 |
| Proteose peptone[1] | 0.001–0.1 |
| Carbon source | 3.0–50.0 |

[1]These materials were commercially obtained from Difco, Detroit, Michigan.

Cultures are typically grown on such a medium at a temperature of about 30° C. in conventional shaker flasks or other fermentation apparatus for at least about 10–14 days. The fungus is then harvested and recovered, for example by centrifugation. The starch-degrading enzyme mixture produced by the fungus remains in the culture medium from which it may be recovered. One method for so recovering the enzyme mixture involves precipitating the mixture from the medium by adding a suitable precipitation-effecting material, for example, a 75% saturated solution of ammonium sulfate or acetone.

It has been found that enzyme production is enhanced in the presence of a surfactant. It is therefore desirable that a surfactant, for example, a polyoxyethylene derivative of a fatty acid partial ester of a sorbitol anhydride such as Tween-80 manufactured by Atlas Chemical Industries, Inc., be added to the growth medium. Suitable amounts of the surfactant are amounts in the range 0.01 to 1.0 percent.

Alternative media for growing the *Cladosporium resinae* include corn steep liquor which is commonly used for culturing fungi to obtain extracellular enzymes produced thereby. High yield of the fungus may also be obtained by growing the fungus on solid media, for example, wheat bran and extracting the enzymes from the culture media using water or a salt solution.

More particularly, the fungus has been grown in a medium containing 1.0% $KH_2PO_4$, 0.14% $(NH_4)_2SO_4$, 0.03% urea, 0.03% $MgSO_4 \cdot 7H_2O$, 0.03% $CaCl_2$, 0.10% proteose peptone and 1 ml per liter of a trace metal solution containing 500 mg $FeSO_4 \cdot 7H_2O$, 150 mg MnSO$_4$.H$_2$O, 160 mg ZnCl$_2$, 200 mg CoCl$_2$ and 1 ml of 19% HCl per 100 ml of water. To this mineral solution, carbohydrate was added to a final concentration of 0.5–0.8% and the pH adjusted to 5.3.

The fungus was then grown on slants composed of the aforementioned mineral solution containing 0.5% w/v glucose and 3% w/v agar. The entire culture on a single slant was transferred to 200 ml of culture solution containing 0.5% glucose as the carbon source. After a 3 day growth period, aliquots (10 ml) of this culture were added to 250 ml flasks containing 50 ml of culture solution either at different pH values or containing different carbon sources or different mineral element levels. These cultures were grown in a controlled environment incubator shaker at 30° C. for up to 21 days. Aliquots were removed at approximately 3 day intervals, centrifuged to remove mycelium, dialyzed overnight against distilled water and then assayed for activity against starch and pullulan.

Alternatively, aliquots (5 ml of the 3 day glucose culture were used to inoculate bran medium. This wheat bran medium was prepared by kneading wheat bran (15 g) and distilled water (10 ml) in a 250 ml Erlemeyer flask. All cultures were autoclaved at 15 psi and 121° C. for 15 minutes. After inoculation the wheat bran cultures were incubated at 30° C. for up to 20 days. The bran was extracted with 60 ml of a NaCl solution (1.5%) containing 2–3 drops of Tween-80. After addition of the NaCl solution the slurry was allowed to stand at 30° C. for 5 hours. The culture was then filtered through cheesecloth and the bran extracted with another 40 ml of NaCl solution. The combined extracts were centrifuged and dialyzed against distilled water for 18 hours.

When *Cladosporium resinae* was grown in solution culture with glucose as the carbon source there was vigorous growth in the first three days but little enzyme production. Enzyme production increased significantly over a culture period of 20 days as shown in FIG. 1 even though most of the carbohydrate was utilized in the first three days of growth.

In initial experiments with this organism the amounts of glucoamylase enzymes produced were greatly affected by the nature of the carbon source used in the culture medium. Thus, significantly more enzyme was produced when the carbohydrate employed was starch or pullulan than when glucose or maltose was employed. This is shown in Table I.

TABLE I

PRODUCTION OF *CLADOSPORIUM RESINAE* ENZYMES IN LIQUID CULTURE

| Carbon Source | Activity (U/ml) | |
|---|---|---|
| | Starch | Pullulan |
| Glucose | 0.42 | 0.05 |
| Maltose | 0.39 | 0.05 |
| Starch | 0.36 | 0.03 |
| Pullulan | 0.73 | 0.16 |

However, on continued culturing of this organism over several months several levels of enzyme were produced independent of the carbohydrate used as the carbon source as shown in Table II. Optimal enzyme production was attained when the phosphate level was 1.0%. Lower levels of phosphate resulted in lower enzyme production and more sporadic results. Urea could be replaced by equivalent amounts of (NH$_4$)$_2$SO$_4$ with little effect on enzyme production.

TABLE II

PRODUCTION OF *CLADOSPORIUM RESINAE* ENZYMES IN LIQUID CULTURE

| Carbon Source | Activity (U/ml) | |
|---|---|---|
| | Starch | Pullulan |
| Glucose (0.5%) | 1.6 | 0.23 |
| Starch (0.5%) | 1.1 | 0.14 |
| Starch (0.5%) + Glucose (0.3%) | 1.9 | 0.26 |
| Pullulan (0.5%) | 0.9 | 0.18 |
| Pullulan (0.5%) + Glucose (0.3%) | 1.5 | 0.24 |
| Maltose (0.5%) | 1.4 | 0.20 |
| Nigeran (0.5%) | 0.5 | 0.09 |
| Polyporus Betulinus Glucan (0.5%) | 0.6 | 0.10 |

50 ml culture solution inoculated with 10 ml of a 3 day glucose culture, then grown at 30° C. for 17 days on a rotary incubator.

When *Cladosporium resinae* was grown on a wheat bran solid culture, considerably more enzyme was produced as shown in Table III. Maximal levels of enzyme were attained after 11 days growth and when a fresh glucose culture was used to inoculate the bran.

TABLE III

PRODUCTION OF *CLADOSPORIUM RESINAE* ENZYMES IN SOLID CULTURE

| Days of Growth | Activity (U) | |
|---|---|---|
| | Starch | Pullulan |
| 7 | 460 | 80 |
| 13 | 1350 | 210 |
| 19 | 1550 | 230 |

Wheat bran (15 g) plus water (10 ml) in 250 ml flasks, sterilized and inoculated with 5 ml of 3 day glucose cultures followed by incubation at 30°. The cultures were then extracted with 60 ml of NaCl (1.5%) containing Tween 80 (0.4%), and then by a further 30 ml of NaCl (1.5%).

The enzyme preparation has sometimes been found to possess a transferase activity similar to that produced by *Aspergillus niger*. This transferase activity may be removed by binding to inorganic materials such as bentonite. Except for the removal of the transferase when necessary, it is expected that the enzyme preparation will, for the most part, be used without fractionation although the levels of individual components might be varied to advantage by culturing the organism under different conditions, e.g., by using different carbon sources.

The component enzymes of the mixture of starch-degrading enzymes produced by *Cladosporium resinae* can be separated therefrom. Thus, for example, an ammonium sulfate precitate containing the mixture and obtained by adding saturated ammonium sulfate to a liquid medium can be fractionated by chromatography on DEAE-cellulose and Sephadex C-100. At least four enzymes can be recovered in substantially homogeneous form, namely, an α-amylase which has no action on pullulan, a maltase (α-glucosidase) having high activity on maltose but no action on pullulan, a glucoamylase similar in substrate specificity to glucoamylase obtained from *Aspergillus niger*. This glucoamylase sometimes appears as two fractions during separation but it is believed that only one enzyme is present. This enzyme is referred to herein as glucoamylase S. The fourth enzyme is also a glucoamylase-type enzyme which has the ability to degrade pullulan at a rapid rate. This glucoamylase is referred to herein as exopullulanase. This novel exo-pullulanase also hydrolyzes substrates containing α-glucosidic linkages including isomaltose, maltose and amylopectin. The sole or major product of its action on all of these substrates is glucose. The action of exo-pullulanase on partly oxidized amylose or partially oxidized pullulan showed that these polysaccharides were degraded to only limited extents indicating that the action of the enzyme is of an exo-type. Furthermore, the glucose released from starch and pullulan is in the $\beta$-form as would be expected of an exo-acting glucohydrolase.

Figure 2:
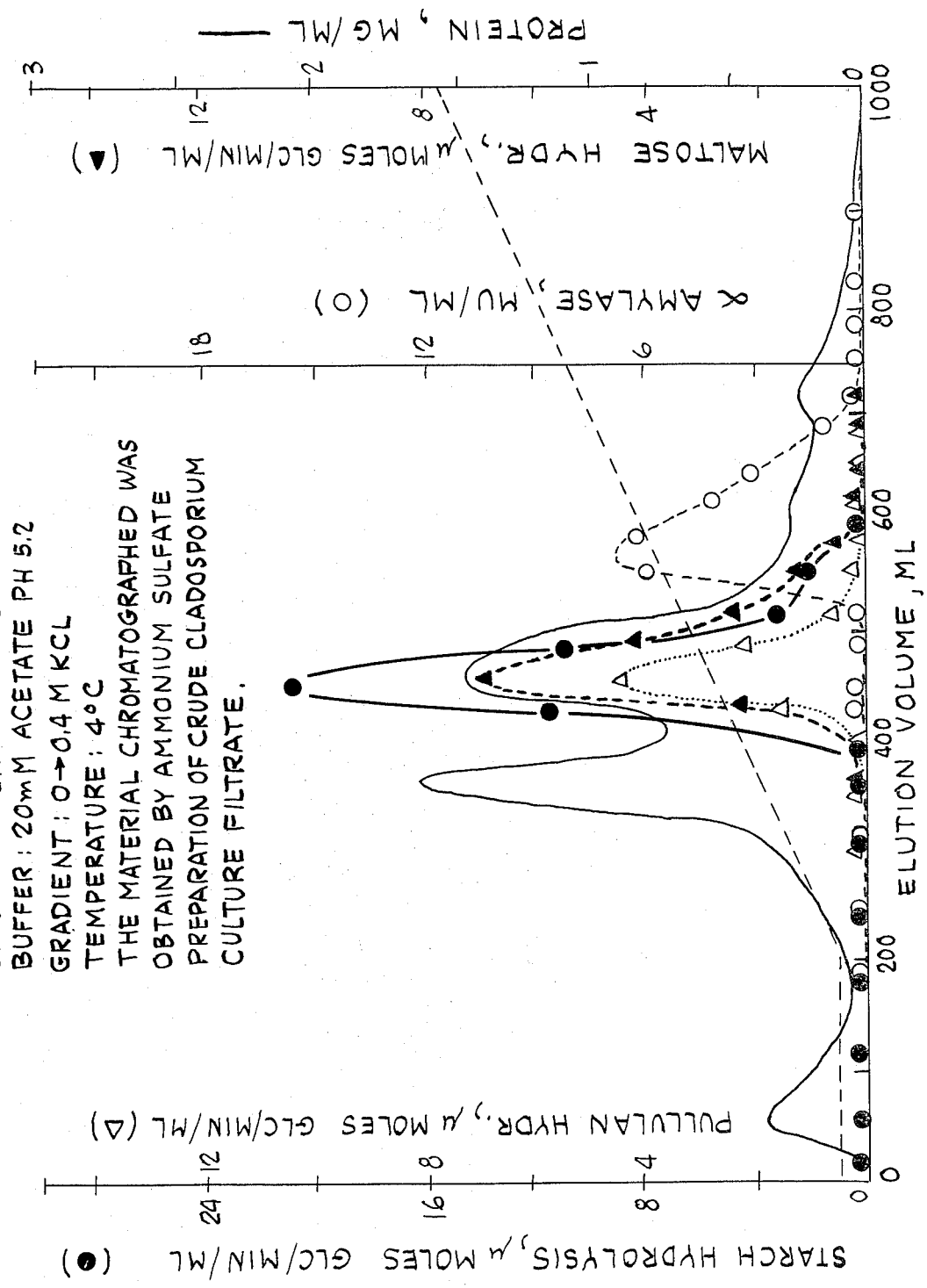
Figure 11:
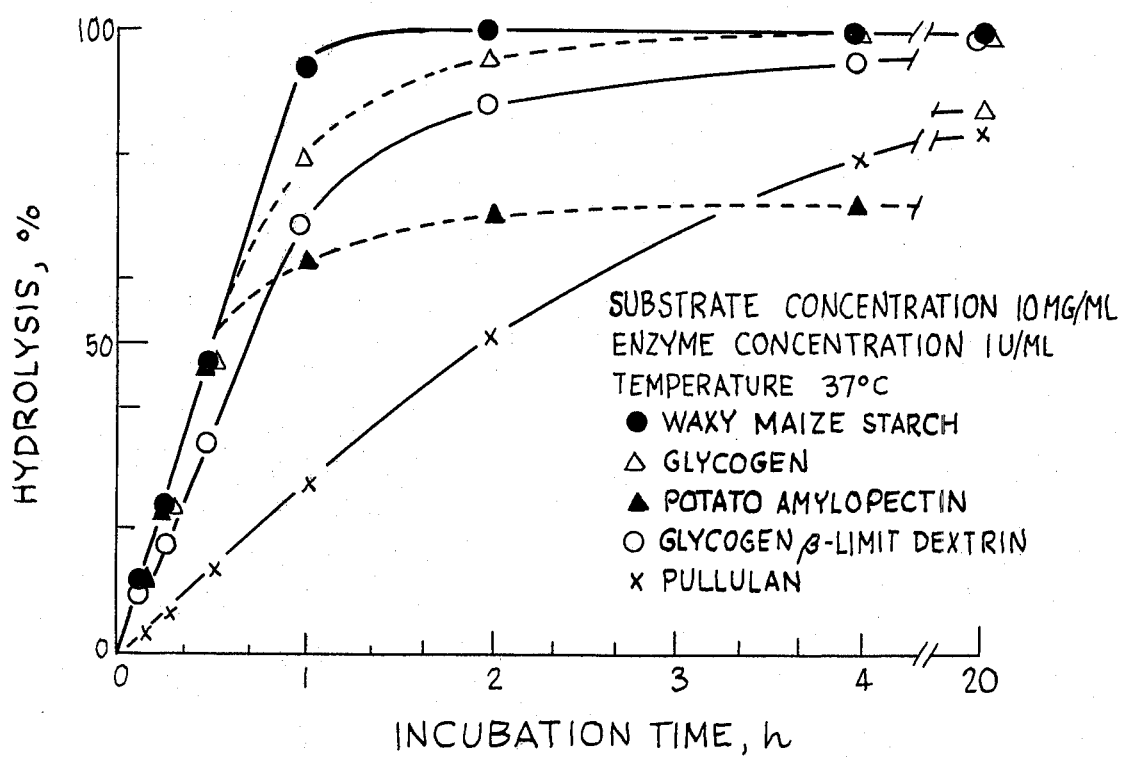

More particularly, crude culture solutions (1 l) were centrifuged at 8,000 g for 20 minutes at 4° C. and solid ammonium sulfate was added to 80% saturation together with 1 g of celite. The resulting precipitate was allowed to settle overnight and the bulk of the supernatant was removed by suction. The remaining solution was centrifuged (8,000 g, 20 minutes) and the recovered pellet was dissolved in H$_2$O (50 ml). Insoluble celite was removed by centrifugation and the supernatant dialyzed for 18 hours at 4° C. against citrate/phosphate buffer (pH 8.0, 0.01 M). This solution was adjusted to pH 5.2, centrifuged and then applied to a DEAE-cellulose column (10 cm×2.5 cm) pre-equilibrated with 10 mM sodium acetate buffer (pH 5.2). The column was washed with the same buffer and the enzyme was eluted using a 0 to 400 mM KCl gradient in 10 mM acetate buffer. Fractions were assayed for glucoamylase action on starch and pullulan, action on maltose and for $\alpha$-amylase enzyme. The results are shown in FIG. 2.

In assaying the rate of release of glucose from starch, pullulan or maltose, enzyme solution (culture solution) (0.1 ml) undiluted or diluted up to 100-fold, was incubated with substrate solution (0.5 ml) for 5 to 20 minutes at 37° C. for 1 hour. This reaction was terminated and the color developed by adding 50% HCl solution (2 ml). Substrates employed were pullulan, maltose and J. T. Baker Starch (Lintner). Soluble all at 5 mg/ml concentration and in 0.1 M sodium acetate buffer pH 4.3. $\alpha$-amylase was assayed by the method described in Marshall, J. J., et al, *Clinica Chemica Acta*, 76, 277 (1977).

By the column chromatographic fractionation, glucoamylase was obtained essentially free of $\alpha$-amylase. The glucoamylase fraction (Fraction I) readily hydrolyzed starch, pullulan and maltose releasing glucose. This fraction was further purified by chromatography on Ultrogel AcA 34 which removed some non-enzyme protein but gave no further fractionation of enzyme activities. However, chromatography of this active glucoamylase fraction in citrate/phosphate buffer (0.1 M, pH 8.0) on a column of Sephadex G-100 (1.y×8.3 cm) resulted in the separation as shown in FIG. 3 of two glucoamylases termed glucoamylase S and exo-pullulanase. Exo-pullulanase has a high relative activity on pullulan (10 mg/ml) whereas glucoamylase S has a relatively low ability to release glucose from pullulan.

At this state of purification glucoamylase S, which apparently has some bio-specific affinity for Sephadex G-100, appeared as a single protein band on SDS- and conventional gel electrophoresis. On isoelectric focusing glucoamylase S was devoid of $\alpha$-amylase activity. The isoelectric focusing was performed as previously described by McCleary B. V., *Phytochemistry, in press.* SDS-gel electrophoresis was performed on an LKB Multiphore according to conventional techniques.

Exo-pullulanase still contained some non-enzyme protein bands which were subsequently removed by chromatography of the enzyme preparation on DEAE-Sepharose at pH 8 (citrate/phosphate). This step also removed remaining traces of $\alpha$-amylase. The enzyme was applied to the column (1.6×5.5 cm) in 10 mM citrate/phosphate buffer (pH 8) and eluted with a linear KCl gradient (0-400 mM) in the same buffer.

Thus, both enzymes were obtained in essentially homogeneous form as determined by gel electrophoresis and electrofocusing and were devoid of $\alpha$-amylase contamination.

Fraction II recovered from the DEAE-cellulose chromatography step contained $\alpha$-amylase activity in addition to maltose-degrading activity. This fraction after concentration was chromatographed on Ultrogel AcA 34 (2.5×8.5 cm) and eluted with 10 mM citrate/phosphate buffer pH 8.0.

As shown in FIG. 4, two major peaks of activity were separated, one with high activity on maltose, termed a maltase enzyme, and the other being a mixture of $\alpha$-amylase and the two glucoamylases, that is, glucoamylase S and exo-pullulanase. The maltase enzyme was further purified by chromatography on a DEAE-Sepharose column (1.6×5.5 cm). The enzyme was applied in 10 mM citrate/phosphate buffer (pH 8.0) and eluted with a linear KCl gradient (0-400 mM KCl) in the same buffer. The maltase enzyme so recovered was homogeneous as determined by gel electrophoresis.

Table IV sets forth the purification procedure in detail for glucoamylase S and exo-pullulanase and indicates the increasing specific activity obtained during purification.

The exo-pullulanase is an unusual glucoamylase as it readily hydrolyzes 1,6-linkages in pullulan. It was possible that this enzyme might actually be a mixture of endo-pullulanase and glucoamylase. To eliminate this possibility the activity of the enzyme on pullulan and carboxymethyl-pullulan was studied and the results are shown in FIG. 5.

TABLE IV

PURIFICATION OF *CLADOSPORIUM RESINAE* GLUCOAMYLASE S AND EXO-PULLULANASE

| STEP | Protein (mg) | Activity (U) | Specific Activity (U/mg) | Recovery | Purification |
|---|---|---|---|---|---|
| Crude culture filtrate (1 l of culture filtrate from 10 l fermentation) | 5856 | 1100 | 0.17 | 100 | 1 |
| Ammonium sulfate Precipitate (80% Satn.) | 2684 | 1090 | 0.41 | 99 | 2.4 |
| DEAE-cellulose | 129 | 1020 | 7.9 | 93 | 46 |
| Ultragel AcA34 | 43 | 865 | 20.3 | 78 | 119 |
| Sephadex G-100 (Exo-pull.) | 19 | 345 | 17.9 | 31 | 105 |
| (S) | 13 | 350 | 27.3 | 32 | 161 |
| DEAE-Sepharose (Exo-pull.) | 10 | 280 | 27.0 | 25 | 159 |

Carboxymethyl-pullulan was prepared as follows. To a solution of pullulan (10 g) in water (200 ml) at 70° C. sodium sulphate (66.6 g) was added. On dissolution, monochloroacetic acid (1.1 g) in H$_2$O (5 ml) was added. This was followed by the slow addition of NaOH (1.3 g) in H$_2$O (10 ml). The solution was stirred at 70° C. for 1.5 hour, and then the carboxymethyl-pullulan was recovered by filtration, dissolved in hot water (200 ml) and dialyzed against running tap water for 24 hours. The resulting solution was freeze dried. The degree of substitution (carboxymethylation) was determined according to the procedure of Thewlis, B. H., *Die Starke*, 21,21 (1969) and found to be 0.2.

To determine the mode of action of exo-pullulanase on pullulan and carboxymethyl-pullulan, the substrate (2 ml, 5 mg/ml) was incubated with exo-pullulanase (0.1 mg, 1.0 M) at 37° C. Samples (0.2 ml) were taken at various time intervals up to 6 hours and diluted to 2.0 ml. From this, aliquots (0.1 ml) were taken for the determination of glucose by the glucose oxidase procedure described in Lloyd, J. B. and Whelen, W. J., *Anal. Biochem.*, 30, 467 (1969), and for the determination of total carbohydrate by the phenol-sulfuric acid method of Dubois, M., et al., *Anal. Chem.* 28, 350 (1950).

It was found that a slight substitution of pullulan with carboxymethyl groups greatly limits the degree of hydrolysis of this substrate by the exo-pullulanase, thus confirming that the enzyme acts as a typical glucoamylase removing single glucosyl residues from the non-reducing end of the polysaccharide. Studies with a highly purified pullulanase obtained from Hayashibara Biochemical Labs, Inc., Okayama, Japan, showed that this enzyme readily hydrolyzed both the pullulan and the carboxymethyl pullulan thus indicating that the degree of substitution was not sufficient to hinder endo-pullulanase activity.

The relative rates of hydrolysis of several glucooligosaccharides and polysaccharides are shown in Table V based upon data shown in FIGS. 6-11. Results are compared to those obtained using *Aspergillus niger* glucoamylase II. All three enzymes readily hydrolyze starch, amylopectin and glycogen but exo-pullulanase is much more effective in hydrolyzing β-limit glycogen than are the other two enzymes. This difference and the greater relative rates of hydrolysis of pullulan and isomaltose by exo-pullulanase than by glucoamylase S, *Asperigillus niger* glucoamylase or by glucoamylases studied by others clearly demonstrates the greater ability of the former enzyme to cleave 1-6-linkages in the oligo- and polysaccharides. Table VI provides the kinetic constants of the *Cladosporium resinae* glucoamylases and *Asperigillus niger* glucoamylase.

TABLE V

RELATIVE RATES OF SUBSTRATE HYDROLYSIS BY
*CLADOSPORIUM RESINAE* AND *ASPERGILLUS NIGER* GLUCOAMYLASES

| SUBSTRATE | *CLADOSPORIUM RESINAE* EXO-PULLULANASE | *CLADOSPORIUM RESINAE* GLUCOAMYLASE S | *ASPERGILLUS NIGER* GLUCOAMYLASE II |
|---|---|---|---|
| Soluble Starch | 100 | 100 | 100 |
| Potato amycopectin | 100 | 100 | 100 |
| Waxy maize starch | 100 | 100 | 100 |
| Glycogen | 100 | 100 | 96 |
| Glycogen β-limit Dextrin | 78 | 44 | 41 |
| Pullulan | 39 | 3 | 1.5 |
| Maltose | 22 | 10 | 18 |
| Isomaltose | 4 | 0.05 | Not tested |
| Dextran | 2 | 0.03 | Not tested |

Activities were determined in solutions containing substrate at a concentration of 8.3 mg/ml.

TABLE VI

KINETIC CONSTANTS OF *CLADSPORIUM RESINAE* GLUCOAMYLASES

| SUBSTRATE | *CLADOSPORIUM RESINAE* EXO-PULLULANASE | | *CLADOSPORIUM RESINAE* GLUCOAMYLASE S | | *ASPERGILLUS NIGER* GLUCOAMYLASE II | |
|---|---|---|---|---|---|---|
| | $K_M$ | $V_{MAX}$ | $K_M$ | $V_{MAX}$ | $K_M$ | $V_{MAX}$ |
| Soluble starch | 0.007 | 28.2 | 0.007 | 29.0 | 0.9 | 26.0 |
| Waxy maize starch | 0.007 | 28.2 | 0.007 | 29.0 | 0.5 | 26.0 |
| Potato amylopectin | 0.007 | 28.2 | 0.007 | 29.0 | 0.5 | 26.0 |
| Glycogen | 0.03 | 28.2 | 0.03 | 29.0 | 1.7 | 25.0 |
| Glycogen β-limit dextrin | 0.03 | 22.0 | 0.05 | 15.0 | 5.6 | 11.0 |
| Pullulan | 0.58 | 10.8 | 150.0 | | 150.0 | 4.0 |
| Maltose | 0.80 | 7.4 | 1.40 | 2.9 | 0.5 | 4.8 |
| Isomaltose | 16.7 | 2.6 | | | | |

$V_{MAX}$ Values are μmoles glucose released per min per mg protein.
$K_M$ Values are mg/ml.

The physio-chemical properties of the *Cladosporium resinae* enzymes, glucoamylase S and exo-pullulanase, are set forth in Table VII including molecular weight, optimal pH and temperature and pH and temperature stability of the enzymes in comparison with *Aspergillus niger* glucoamylase II.

TABLE VII

PROPERTIES OF *CLADOSPORIUM RESINAE* GLUCOAMYLASES

| PROPERTY | *CLADOSPORIUM RESINAE* EXO-PULLULANASE | *CLADOSPORIUM RESINAE* GLUCOAMYLASE S | *ASPERGILLUS NIGER* GLUCOAMYLASE II |
|---|---|---|---|
| Mol. wt. | 70,000 | 82,000 | 71,000 |
| PI | 4.5 | 4.3 | 4.1 |
| Carbohydrate (%) | 4.6 | 8.2 | 14.4 |
| pH optimum | 3.5-4.0 | 3.5 | 4.0-4.5 |
| pH stability (37° C., 20 hours) | 4.0-7.0 | 4.0-6.0 | 3.5-7.0 |
| Temperature optimum | 60° C. | 60° C. | 60° C. |
| Temperature stability | Up to 55° C. | Up to 48° C. | Up to 55° C. |

TABLE VII-continued
PROPERTIES OF CLADOSPORIUM RESINAE GLUCOAMYLASES

| PROPERTY | CLADOSPORIUM RESINAE EXO-PULLULANASE | CLADOSPORIUM RESINAE GLUCOAMYLASE S | ASPERGILLUS NIGER GLUCOAMYLASE II |
|---|---|---|---|
| (pH 4.3, 10 min.) | | | |

The relative rates of hydrolysis of glycoamylase from Aspergillus niger and exo-pullulanase are also compared in Table VIII, wherein exo-pullulanase is seen to have much greater ability to cleave the 1,6-linkages in isomaltose, panose, isomaltotriose and dextran.

TABLE VIII

Relative Rates of Substrate Hydrolysis by Aspergillus niger Glucoamylase and Cladosporium resinae "exo-pullulanase" (expressed relative to amylopectin as 100).

| Substrate | Cladosporium | Aspergillus |
|---|---|---|
| Amylopectin | 100 | 100 |
| Amylopectin β-limit dextrin | 74 | 60 |
| Maltose | 25 | 21 |
| Panose | 24 | 4.8 |
| Pullulan | 20 | 0.3 |
| Isomlatotriose | 3.9 | 0.6 |
| Isolichenin | 2.2 | 0.5 |
| Isomaltose | 2.1 | 0.2 |
| Nigerose | 0.6 | 0.2 |
| Dextran | 0.5 | 0.03 |

The mixture of starch-degrading enzymes is believed to function in the conversion process as follows. α-Amylase serves to enable the exo-acting glucanase to bypass structural anomalies in the substrate, helping to insure that maximum hydrolysis is achieved. The Aspergillus-type glucoamylase help to convert linear chains in the substrate into glucose when unhindered by 1,6-linkages. α-Glucosidase has good activity toward isomaltose and hydrolyzes this disaccharide which is produced as a by-product by reversion reactions. The novel exo-pullulanase plays the most important part in starch conversion processes, as it degrades the macromolecular substrate at a fast rate irrespective of the presence of branch points. Using the mixture of starch-degrading enzymes the conversion into glucose can be brought about in a much shorter period of time than with Aspergillus niger enzyme preparations.

Comparative studies of the conversion of amylopectin into glucose using Aspergillus niger glucoamylase and either the mixture of starch-degrading enzymes or the exo-pullulanase were carried out. When used at the same concentration (measured in terms of ability to release glucose from starch) the mixture or the exo-pullulanase bring about conversion of substrate in about 1/5 to 1/10 of the time which the Aspergillus niger enzyme requires to effect the same degree of conversion. Final extents of conversion are: Aspergillus enzyme, 92%; mixture 98%; and exo-pullulanase, 95%.

The mixture of starch-degrading enzymes from Cladosporium resinae (ATCC No. 20495) or the exo-pullulanase can be used for the manufacture of dextrose from starch. Starch is preferably first solubilized by acid, enzyme, or acid/enzyme treatment. The concentration of the resulting "solution" should be as high as possible, e.g. 25-30%, and the Dextran Equivalent (DE) of the solubilized starch as low as possible, e.g. 0.5-5, while still maintaining satisfactory rheological properties. The pH of the solution should be in the range 1.5-8.5, preferably 3-4.5.

An amount of the enzyme, either the mixture or the exo-pullulanase, sufficient to convert substantially all of the starch, is added to the solubilized starch. The exact amount of either material which is required depends upon the enzyme preparation used, although amounts in the range 1-30 International Units of activity per milliliter of reaction mixture are usually employed (1International Unit of activity is the amount that releases 1 μmole of glucose per minute at 37° C. under optimal conditions of starch degradation). For the mixture, use of a final concentration of 5 International Units of activity per milliliter of reaction mixture will typically bring about 95-100% conversion in about 20 hours. Suitable temperatures are in the range 30°-70° C., preferably less than about 55° C., because the enzyme is slightly less thermostable than the Aspergillus enzyme. The enzyme preparation can be modified by immobilization or other means in such a way as to increase thermostability, e.g. on DEAE-cellulose or inorganic carriers. After the conversion is complete the process is completed by standard procedures, e.g., enzyme inactivation, decolorization, crystallization, and removal of the crystallized enzyme.

In addition to its use for the production of dextrose, the enzyme preparation and/or the exo-pullulanase can be used together with glucose isomerase for the production of fructose syrups from starch. The relative thermolability of the enzyme preparation and of the exo-pullulanase renders both preferable to the Aspergillus enzyme in the production of low calorie alcoholic beverages such as beer. When so used, the enzyme or the enzyme mixture increases the fermentability of high DE starch conversion products in the wort thus bringing about a low carbohydrate, low calorie alcoholic product. Then during pasteurization the enzyme or enzyme mixture is inactivated so that it does not appear in an active form in the final product.

Some distinct advantages of the Cladosporium resinae preparation over the Aspergillus niger enzyme in starch conversion include: the ability of one of the Cladosporium resinae constituents of the enzyme mixture to readily cleave the α-1,6-glucosidic linkages in starch increases the rate and extent of conversion of starch into dextrose over that obtained with the Aspergillus niger enzyme; the Cladosporium resinae enzyme can be used at lower pH; the presence of an α-glucosidase in Cladosporium resinae causes breakdown of reversion products, e.g. isomaltose; and the thermolability is advantageous in the case where amylolytic enzymes are to be used for increasing wort fermentability, e.g., in the production of low calorie beers.

As will be clear to anyone skilled in the art, many variations, modifications and alterations may be made in the invention without departing from the spirit and scope thereof as set forth in the preceding description or in the claims which follow.

What is claimed is:

1. A method of producing a low calorie alcoholic beverage which comprises contacting or incorporating in a fermentation wort a mixture of starch-degrading enzymes recovered from the culturing of Cladosporium

*resinae* (ATCC No. 20495) in a growth medium containing an assimilable carbon source and other nutrients.

2. A method in accordance with claim 1 wherein said mixture of starch-degrading enzymes includes an exo-pullulanase, a maltase, an alpha-amylase and glucoamylase S.

3. A method of producing a low calorie alcoholic beverage which comprises incorporating in a fermentation wort the enzyme exo-pullulanase recovered from the mixture of starch-degrading enzymes produced by culturing *Cladosporium resinae* (ATCC No. 20495) so as to increase the fermentability of DE starch conversion products in said wort.

4. A method of producing a low calorie alcoholic beverage which comprises incorporating in a fermentation wort the enzyme glucoamylase S recovered from the mixture of starch-degrading enzymes produced by culturing *Cladosporium resinae* (ATCC No. 20495).

* * * * *